(12) United States Patent
Bartel

(10) Patent No.: US 8,182,478 B2
(45) Date of Patent: May 22, 2012

(54) ELECTROSURGICAL INSTRUMENT AND TYPE SERIES FOR ELECTROSURGICAL INSTRUMENTS

(75) Inventor: Volker Bartel, Bodelshausen (DE)

(73) Assignee: ERBE Elektromedizin GmbH, Tübingen (DE)

( * ) Notice: Subject to any disclaimer, the term of this patent is extended or adjusted under 35 U.S.C. 154(b) by 898 days.

(21) Appl. No.: 12/279,377

(22) PCT Filed: Feb. 12, 2007

(86) PCT No.: PCT/EP2007/001196
§ 371 (c)(1),
(2), (4) Date: Aug. 14, 2008

(87) PCT Pub. No.: WO2007/093351
PCT Pub. Date: Aug. 23, 2007

(65) Prior Publication Data
US 2009/0209959 A1 Aug. 20, 2009

(30) Foreign Application Priority Data
Feb. 14, 2006 (DE) .................... 10 2006 006 812

(51) Int. Cl.
*A61B 18/18* (2006.01)
(52) U.S. Cl. .............. 606/37; 606/49; 606/208; 606/50; 606/48
(58) Field of Classification Search ............ 30/175, 30/181, 183, 185, 191, 193; 606/37, 39, 606/40, 41, 45, 48–51, 206, 208
See application file for complete search history.

(56) References Cited

U.S. PATENT DOCUMENTS

| | | | |
|---|---|---|---|
| 1,455,297 A * | 5/1923 | Lyons et al. ................ 30/192 |
| 3,651,811 A * | 3/1972 | Hildebrandt et al. ........... 606/51 |
| 5,324,289 A | 6/1994 | Eggers |
| 6,406,475 B1 | 6/2002 | Wenzler et al. |
| 2004/0006340 A1 | 1/2004 | Latterell et al. |
| 2004/0249374 A1 | 12/2004 | Tetzlaff et al. |

FOREIGN PATENT DOCUMENTS

| | | |
|---|---|---|
| DE | 19929682 | 2/2000 |
| DE | 202004004325 | 5/2004 |
| DE | 202004010780 | 9/2004 |
| EP | 0904738 | 3/1999 |
| EP | 1011484 | 6/2000 |
| EP | 1532932 | 5/2005 |
| EP | 1568330 | 8/2005 |
| JP | 08154491 | 6/1996 |
| WO | WO-97/12558 | 4/1997 |

OTHER PUBLICATIONS

International Preliminary Report on Patentability issued by the International Bureau of WIPO for International Application No. PCT/EP2007/001196, dated Sep. 9, 2008 (English translation).

* cited by examiner

*Primary Examiner* — Jackie Ho
*Assistant Examiner* — Leah Stohr
(74) *Attorney, Agent, or Firm* — Dickstein Shapiro LLP

(57) ABSTRACT

The invention relates to a bipolar electrosurgical instrument comprising a handle and a tool head. In the case of bipolar instruments, at least two mutually separate conducting paths must be provided within the instrument to supply the bipolar tool head. Reliable electrical insulation of these conducting paths relative to one another is often associated with a high cost in known electrosurgical instruments, such as scissors and clamps, since these instruments have a crossed joint. The present invention solves this problem in that the tool head is connected to the handle without crossing over itself.

17 Claims, 4 Drawing Sheets

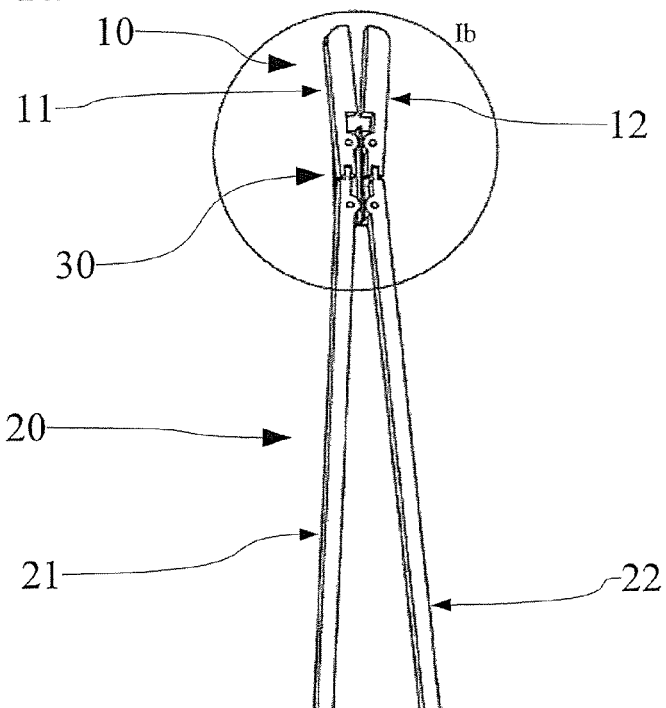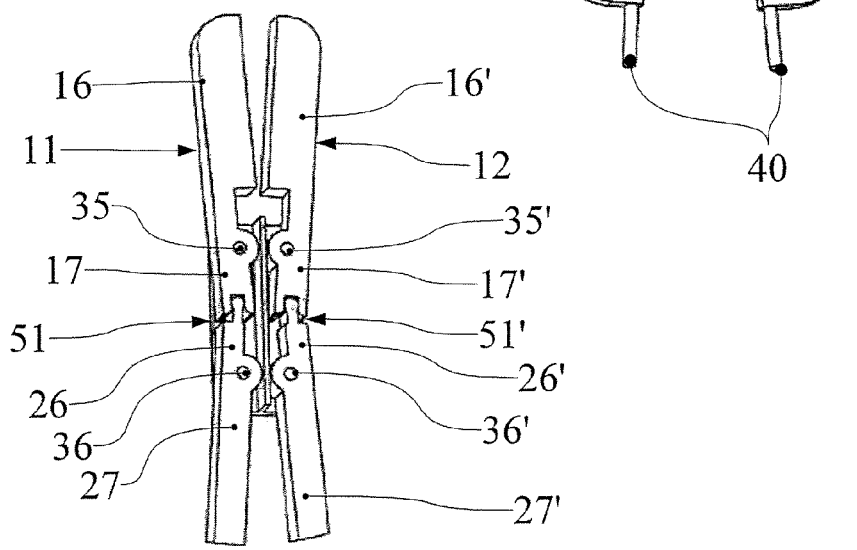

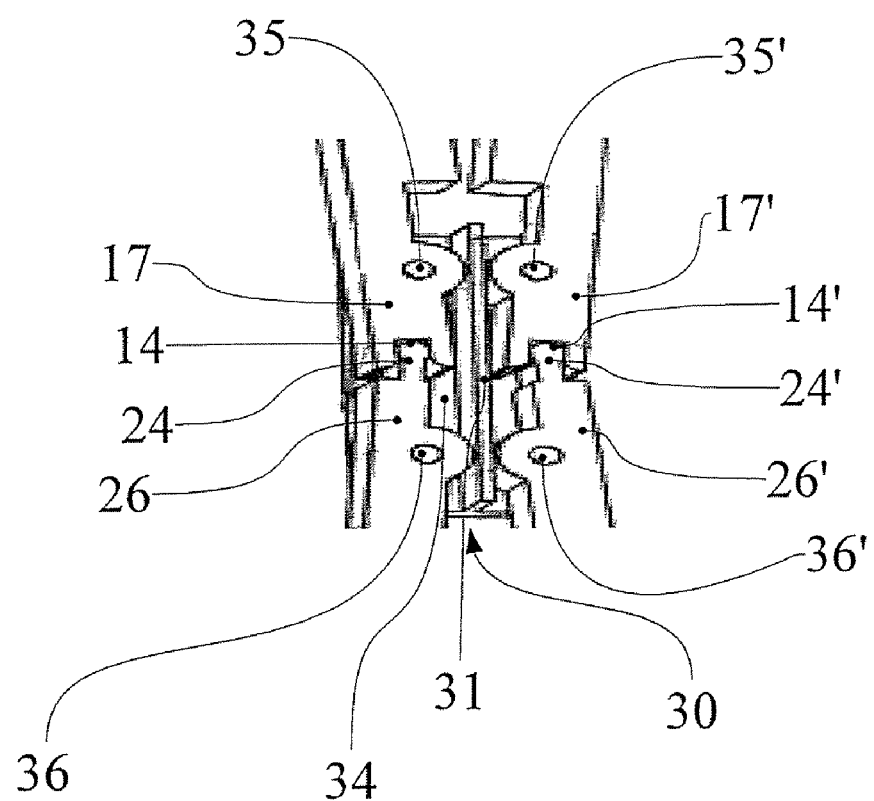

ELECTROSURGICAL INSTRUMENT AND TYPE SERIES FOR ELECTROSURGICAL INSTRUMENTS

BACKGROUND OF THE INVENTION

The invention relates to an electrosurgical instrument.

In high-frequency surgery (HF surgery), alternating current is conducted at high frequency through the human body in order to damage or cut tissue in a targeted manner. An essential advantage over conventional cutting techniques with a scalpel is that, simultaneous with the cutting, suppression of bleeding can take place by closing the affected vessels (coagulation). A distinction is made between a high-frequency generator, which generates the relevant alternating current, and the electrosurgical instrument by means of which the current is applied to the tissue. The electrosurgical instruments which are frequently used are electrosurgical scissors and electrosurgical clamps. These instruments perform a certain double function, since they provide both conventional mechanical clamping and cutting and electrical coagulation and cutting by means of the high-frequency currents.

The electrosurgical instruments described above belong to the class of bipolar electrosurgical instruments. The tool heads of the relevant instruments have two poles between which the alternating current flows. Taking the example of electrosurgical scissors, a first blade can be supplied with the current in a manner that is electrically separated from a second blade. The circuit is completed between the two blades by the tissue to be cut. In order to ensure good functioning of these bipolar electrosurgical instruments, reliable insulation of the electrical conducting paths in the corresponding electrosurgical instruments is necessary. In this regard, the mechanical joints of conventional electrosurgical instruments prove to be particularly problematic since crossing-over and contacting of the relevant conducting paths occurs at the mechanical joints.

The electrosurgical instruments described above are sufficiently well known from U.S. Pat. No. 6,406,475 B1 and U.S. Pat. No. 5,324,289. In order to separate the respective conducting paths from one another, it is proposed therein that insulation be provided at the mechanical joints. For reliable insulation of the two conducting paths, high demands are placed on the form of insulation, which consequently makes production complex and expensive.

A further disadvantage of known electrosurgical instruments is that process-controlled production of a large product range is very complex and expensive. It may be, for example, that different surgeons place different demands on the associated handles of essentially the same instrument on account of the differing anatomy of their hands.

In light of this prior art, it is an object of the present invention to develop an electrosurgical instrument such that it can be operated reliably and practically and that it can be produced economically and efficiently.

SUMMARY OF THE INVENTION

In particular, the aim is achieved with an electrosurgical instrument comprising a handle with a first handle member and a second handle member and a tool head having a first tool limb and a second tool limb, wherein the first and second tool limbs are each attached with a first pivot joint to an at least partially insulating joint bearing, wherein the first handle member, together with the first tool limb, forms a first conducting path and the second handle member, together with the second tool limb, forms a second conducting path which is electrically separated from the first conducting path. The handle members are each attached with a second pivot joint to the joint bearing without crossing over. The tool limbs are also fastened with the second pivot joints without crossing over, the first tool limb being coupled via a first coupling to the first handle member such that a pivot movement about the second pivot joint of the first handle member results in a contrary rotary movement about the first pivot joint of the first tool limb. The second tool limb is coupled via a second coupling to the second handle member such that a pivot movement about the second pivot joint of the second handle member results in a contrary rotary movement about the first pivot joint of the second tool limb.

A central concept of the invention is that the individual conducting paths of the electrosurgical instrument are arranged adjacent and essentially parallel to one another and are therefore automatically separate from one another. This advantage is achieved by providing additional pivot joints which avoid the need for mechanical crossing of the handle members and the tool limbs. A similar principle of pivot joints and coupling arrangement is known from commercially available bolt cutters. Additionally, by this means, advantageous force transmission between the handle members and the associated tool limbs can be achieved. An arrangement of this type can easily be produced by automated means and ensures reliable separation of the conducting paths.

It is conceivable to mount the first pivot joints and the second pivot joints such that they are each rigidly connected to one another, although the rigid connections of the first pivot joints are freely movable relative to those of the second pivot joints and the tool limbs are connected via a non-elastic coupling to the handle member. It is advantageous, however, if the pivot joints are all rigidly connected to one another. A change in length in the electrosurgical instrument caused by the pivot joints and their movement, which could be problematic during an operation, is thereby avoided. The rigid connection should be chosen such that the pivoting ability of the pivot joints about their respective axes is not influenced.

An advantageous expression of the joint bearing is that it comprises two insulator plates between which the pivot joints are arranged. The axes of the pivot joints are therefore arranged substantially perpendicularly to the insulator plates. The pivot joints can thus be configured in a simple manner, wherein reliable insulation is ensured between the individual pivot joints, in particular between the first pivot joint of the first tool limb against the first pivot joint of the second tool limb and of the second pivot joint of the first handle member against the second pivot joint of the second handle member.

Preferably, an insulator web is provided between the tool limbs and between the handle members in the region of the pivot joints, in order to insulate the conducting paths relative to one another. This insulator web therefore extends substantially parallel to the first and the second conducting paths between the respective first and second pivot joints. The insulation of the conducting paths relative to one another is thereby increased. Furthermore, the first and second coupling can be chosen so that mechanical movement of the first coupling on the second coupling is possible. In order to avoid direct contact, the insulator web can function as a mechanical separation and/or as a type of stopper.

Preferably, the insulator web is connected to the joint bearing, in particular with at least one of the two insulator plates. The T-profile thereby produced can be made easily and in one piece. Together with the second insulator plate, an H-profile is formed wherein, on one side of the insulator web, the first conducting path and, on the other side, the second conducting path, run separately from one another, separated by the insulating H-profile.

Preferably, the electrosurgical instrument comprises a non-conducting synchronisation device, in particular between the two first pivot joints and/or between the second pivot joints, for mechanical coupling of the first pivot joints. The mechanical coupling has the effect that a rotation of the first pivot joint of the first tool limb results in a contrary rotation of the first pivot joint of the second tool limb and vice versa. The synchronisation device therefore ensures that none of the tool limbs can be moved independently of the other. This results in an improved operating capability of the instrument. For the construction of this synchronisation device, inter alia, the insulator web can be used wherein said web preferably has devices for accommodating toothed gears attached to the first pivot joints.

A plurality of conducting paths can be provided in the first and the second handle member, although it is preferable if each handle member comprises an electrical connection for an electrical conducting path.

Preferably, the tool limbs each comprise a groove in which a projection of the handle member engages in order to form the first or the second coupling. The coupling is therefore configured as an open joint wherein, on movement of the tool limb, the projection of the first handle member engages in the groove of the first tool limb and the projection of the second handle member engages in the groove of the second tool limb to different depths. Each coupling can be configured single-toothed.

Alternatively, the pivot joints can comprise toothed gears whose pivot point coincides with the pivot axis of the respective pivot joint. The mutually engaging teeth then serve as the coupling. Herein, the toothed gear of the first pivot joint of the first tool limb engages in the toothed gear of the second pivot joint of the handle member and the toothed gear of the first pivot joint of the second tool limb engages in the toothed gear of the second pivot joint of the second handle member.

Preferably, the couplings are made from electrically conductive material and comprise a part of the first or second conducting path. Therefore the mechanical coupling simultaneously serves as an electrical coupling and the circuit is configured to be simple and reliable.

It is advantageous if the tool head and the handle are made from metal and are partially covered with an insulating layer. The individual parts of the tool head and of the handle are therefore conductive in their interior and can be used, respectively, for forming the first and second conducting paths. The insulating layer provides protection against unwanted electric short-circuits.

According to the invention, the problem as set out above is also solved through a type series for electrosurgical instruments. The type series includes at least two tool heads and/or at least two handles which are mutually connectable via the pivot joints and the coupling.

The concept also exists of providing a type of building block system wherein various different tool heads can be combined with different handles. The connection of these elements is carried out by means of the pivot joints and the couplings.

Preferably the handle members, and particularly a handle member length of the different handles are configured to be different. Therefore, for example, depending on the properties of the handle member, different amounts of pressure can be applied with the same tool head. It is also conceivable that any finger holes on the handle members could be varied in order to produce an instrument specifically for the individual surgeon.

The tool heads preferably comprise at least one tool head for cutting and at least one tool head for clamping. Thus, during machine production, a plurality of similar components can be used for different electrosurgical instruments, such as scissors and clamps. The production process is thereby made more economical and the instruments can be better individualised.

BRIEF DESCRIPTION OF THE DRAWINGS

The invention will now be described in greater detail by reference to exemplary embodiments which are illustrated in the drawings, in which:

FIG. 1a shows an electrosurgical clamp according to the invention;

FIG. 1b shows the tool head of the electrosurgical clamp of FIG. 1a;

FIG. 1c shows a detail view of the joint bearing of the electrosurgical clamp of FIG. 1a;

FIG. 3b shows a detail view of the enclosed coupling bearing of FIG. 3a.

DETAILED DESCRIPTION OF THE INVENTION

Figure 2:
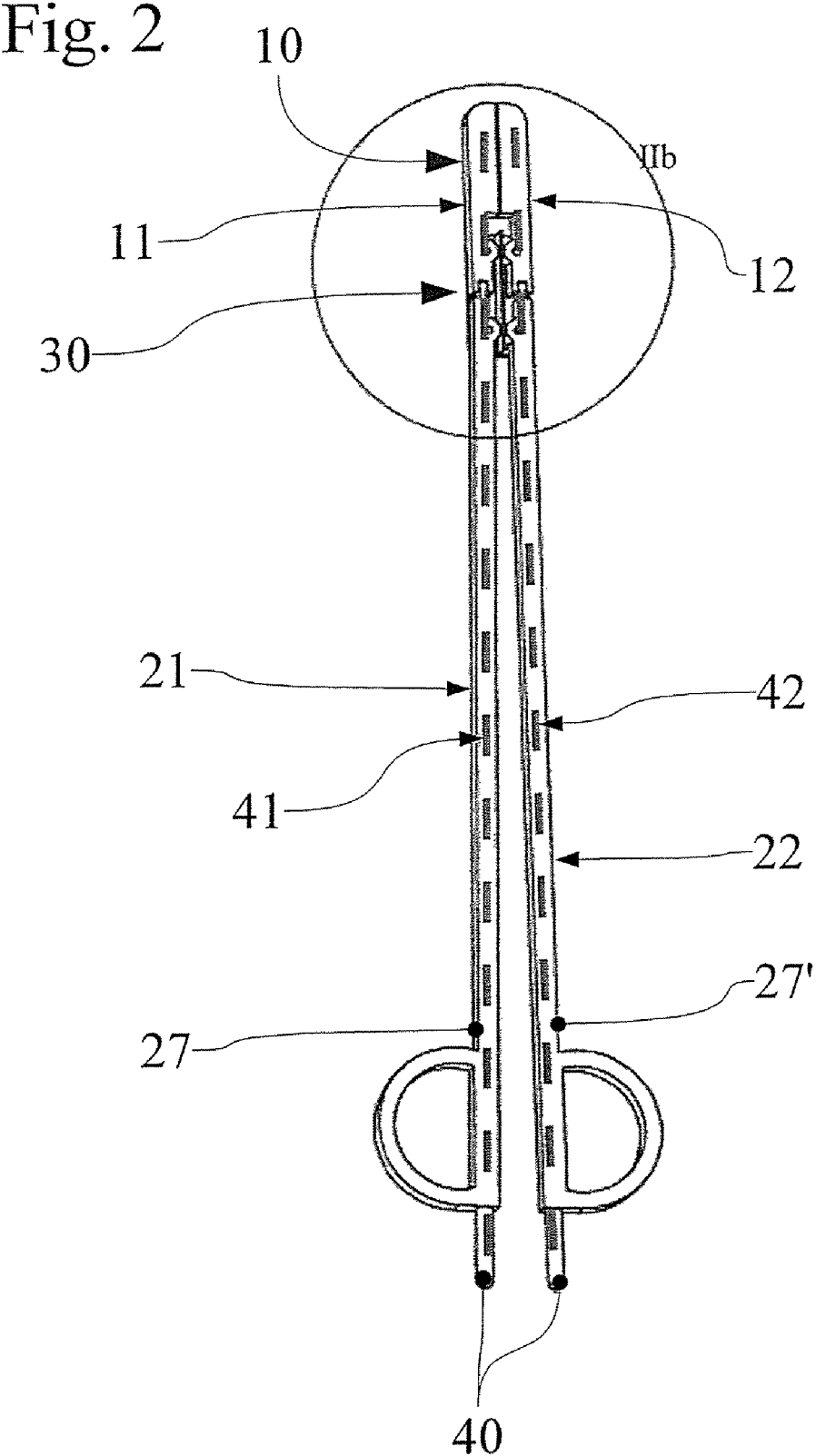
FIG. 2 shows the electrosurgical clamp of FIG. 1a in the closed condition.

In the description below, the same reference signs are used for the same and similarly acting parts.

FIG. 1a shows an electrosurgical clamp according to the invention. The instrument comprises a handle 20 having a first handle member 21 and a second handle member 22 for holding the electrosurgical instrument in the hand and a tool head 10 for grasping and clamping tissue. The handle 20 and the tool head 10 are rigidly connected to one another via an insulating joint bearing 30. In order to elucidate the structure of the joint bearing 30, the joint bearing 30 is shown open in FIGS. 1a, 1b, 1c and 2. The tool head 10 comprises a first tool limb 11 and a second tool limb 12, each of which comprises, on the side remote from the joint bearing, a grasping surface for receiving the tissue. The clamp according to the invention is a bipolar electrosurgical instrument. This means that the tool head 10 or, more precisely, the grasping surfaces, form two mutually electrically separate poles. These poles are connected by means of a first conducting path 41 (see FIG. 2) and a second conducting path 42 to the electrical current circuit of a high frequency generator. As shown schematically in FIG. 2, these conducting paths 41, 42 run separately and parallel along the longitudinal direction of the electrosurgical instrument or the clamp. In order to ensure this, the tool limbs 11, 12 and the handle members 21, 22 are made from electrically conductive material. For the electrical connection to the high frequency generator, the handle members 21, 22 each have an electrical terminal 40.

For the defined movement of the electrosurgical instrument, the clamp has four pivot joints 35, 35', 36, 36' which are mounted on the joint bearing 30 (see FIGS. 1b, 1c). The first tool limb 11 forms around its first pivot joint 35 a rocker-like device. The first pivot joint 35 represents the pivot point about which a front tool section 16 and a rear tool section 17 of the first tool limb 11 are pivotable. This rear tool section 17 is in engagement with a front handle section 26 of the first handle member 21. Similarly to the first tool limb 11, the first handle member 21 also forms a rocker-like device wherein the front handle section 26 and a rear handle section 27 are mounted pivotable about the second pivot joint 36 of the first handle member 21.

The second tool limb 12 and the second handle member 22 are substantially mirror images of the first tool limb 11 and the first handle member 21 and are arranged on the joint bearing 30. The second tool limb 12 therefore comprises a front tool section 16' and a rear tool section 17', which are mounted pivotable about the first pivot joint 35'. The second handle member 22 has on one side of the second pivot joint 36' a front handle section 26' and on the other side a rear tool section 27'. The rear handle section 17' of the second tool limb 12 is in engagement with the front handle section 26' of the second handle member 22.

If the rear handle sections 27, 27' are moved toward one another in this symmetrical arrangement, a rotation movement about the second pivot joints 36, 36' takes place. The rotation movements of the two second pivot joints 36, 36' are directed mutually opposed. By means of a first coupling 51 and a second coupling 51', this rotation movement is inverted and transmitted to both the first pivot joints 35, 35'. The front tool sections 16, 16' are moved toward one another. The tool head 10 is closed.

According to the invention, the force transmission from the first handle member 21 to the first tool limb 11 and from the second handle member 22 to the second tool limb 12 can be adapted for any desired application by variation of the length of the front handle sections 26, 26'. Naturally, the length of the rear tool sections 17, 17' must be chosen accordingly.

According to the invention, the first coupling 51 and the second coupling 51' each comprise a groove 14 or 14' and a projection 24 or 24' which engage in one another (see FIG. 1c). In order, during the rotation movements of the pivot joints 35, 35', 36, 36' described above, to prevent contacting of the first coupling 51 with the second coupling 51', the joint bearing 30 comprises an insulator web 31. This insulator web 31 lies perpendicularly to a bearing base 34 and forms a T-profile therewith. The insulator web 31 extends centrally between the couplings 51, 51' such that contact between said couplings is prevented and the conducting paths 41, 42 are always insulated relative to one another.

Figure 3A:
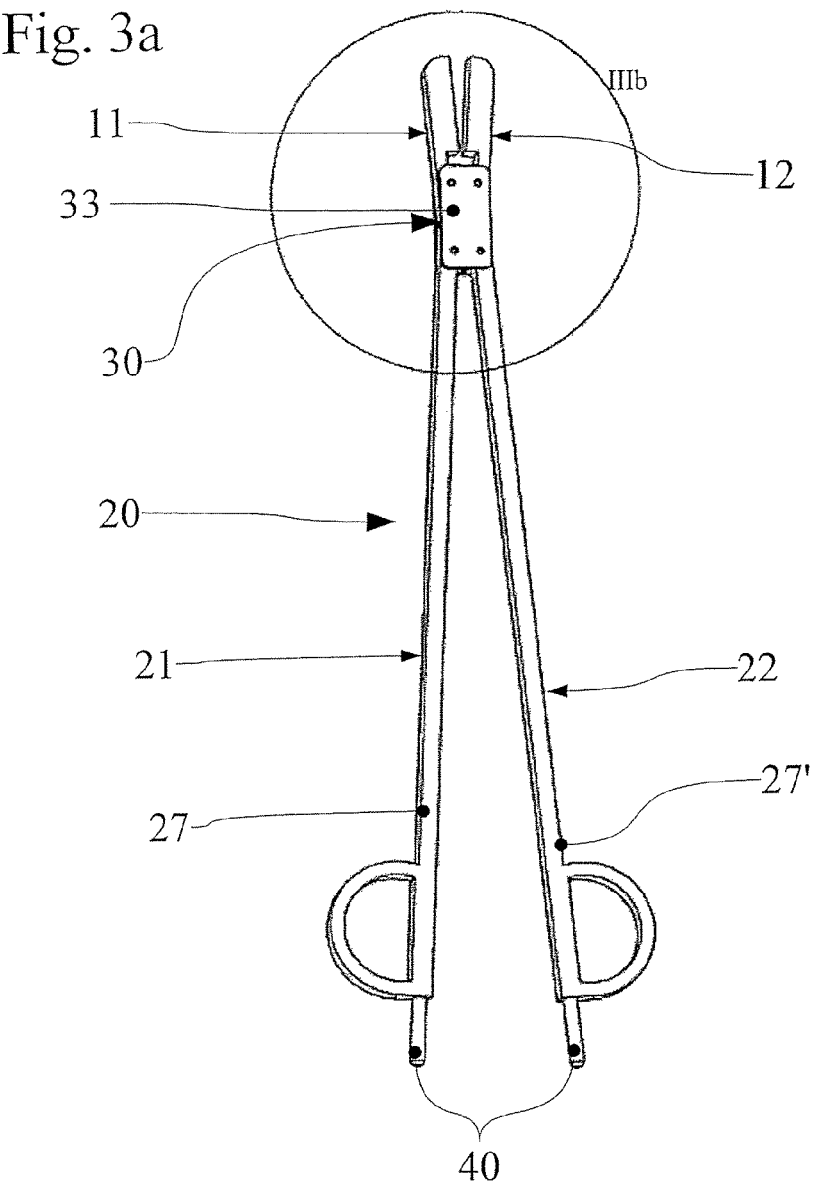
FIG. 3a shows the electrosurgical clamp of FIG. 1a with an enclosed coupling bearing.

FIG. 3a shows the medical clamp according to the invention of FIGS. 1a and 2. However, the joint bearing 30 is enclosed in this case. The enclosure is formed by a bearing cover 33.

Figure 3B:
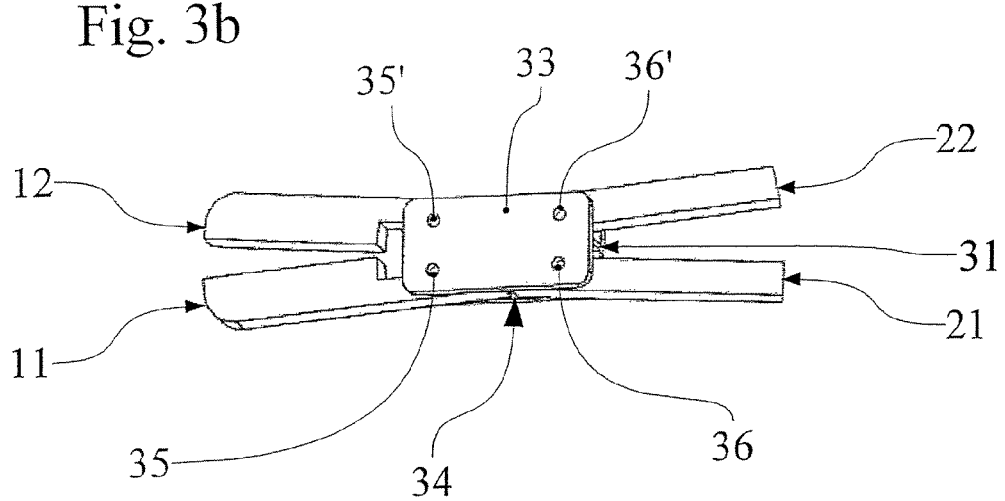

As shown by FIGS. 3a, 3b, the joint bearing 30 comprises the bearing cover 33, the bearing base 34 and the insulator web 31. The bearing cover 33 is arranged parallel to the bearing base 34. In an enclosed condition of the joint bearing 30, these elements therefore comprise an H-profile.

The design of the individual pivot joints 35, 35', 36, 36' is the same in each case. A bolt is fed through an opening in the bearing base 34 through the respective handle member 21, 22 or the respective tool limb 11, 12 to an opening in the bearing cover 33. The tool limbs 11, 12 and handle members 21, 22 are therefore pivotable about the respective bolt. Since the entire joint bearing 30 is made from electrically insulating material, for example plastics, the two conducting paths 41, 42 are electrically screened from one another.

In another exemplary embodiment, the joint bearing 30 is only partially made from electrically insulating material and comprises part of the first and second conducting paths 41, 42. In this exemplary embodiment, the bearing cover 33 has two substantially parallel electrically conductive regions. The first electrically conductive region runs between the first pivot joint 35 of the first tool limb 11 to the second pivot joint 36 of the first handle member 21, the second region runs from the first pivot joint 35' of the second tool limb 12 to the second pivot joint 36' of the second handle member 22. In the first conducting path 41, therefore, the electric current initially flows through the first handle member 21, then in sections through the joint bearing 30 to the first tool limb 11. Similarly, the current flows in the second conducting path 42 through the second handle member 22, a section of the joint bearing 30 and the second tool limb 12. The electrical contact between the tool limbs 11, 12 and the joint bearing 30, in particular the respective electrically conductive region of the bearing cover 33, is created by direct contact and through the bolts of the pivot joints 35, 35', 36, 36'. The electrical contact between the handle members 21, 22 and the joint bearing 30 and the electrically conductive region of the bearing cover 33 is also provided in a similar manner.

In a further exemplary embodiment, the first pivot joints are synchronised. For this purpose, the insulator web 31 is not connected to the remainder of the joint bearing 30. Rather, the insulator web 31 has teeth along its longitudinal direction on both sides in which toothed gears mounted on the first pivot joints 35, 35' engage. On movement of the handle members 21, 22 or the tool limbs 11, 12 coupled thereto, the toothed gears of the first pivot joints 35, 35' rotate about the pivot axis of the pivot joints 35, 35' and displace the insulator web 31 within the joint bearing 30 along the longitudinal direction of the insulator web 31. Each pivot movement of one of the two first pivot joints 35, 35' is therefore automatically transmitted to the other one of the first pivot joints 35, 35'.

In another embodiment, the electrosurgical instrument is constructed substantially identically to the preceding exemplary embodiment. Based on another embodiment of the tool head 10, in particular the front tool sections 16, 16', this electrosurgical instrument is particularly well suited to parting or cutting tissue. As distinct from the previously described electrosurgical clamp, the tool head does not have gripping surfaces, but scissor blades, which enable mechanical cutting. During an operation, the mechanical effects and the electrical effects therefore go together and enable simultaneous parting and eroding or coagulation of tissue.

<center>REFERENCE SIGNS</center>

10 Tool head
11 First tool limb
12 Second tool limb
14, 14' Groove
16, 16' Front tool section
17, 17' Rear tool section
20 Handle
21 First handle member
22 Second handle member
24, 24' Projection
26, 26' Front handle section
27, 27' Rear handle section
30 Joint bearing
30 Insulator web
33 Bearing cover
34 Bearing base
35, 35' First pivot joint
36, 36' Second pivot joint
40 Electrical terminals
41 First conducting path
42 Second conducting path
51 First coupling
51' Second coupling

The invention claimed is:

1. An electrosurgical instrument, comprising
a handle with a first handle member and a second handle member; and
a tool head with a first tool limb and a second tool limb,
wherein the first and second tool limbs are each fastened with respective first pivot joints to an at least partially insulated joint bearing,
the first handle member together with the first tool limb forming a first conducting path
and the second handle member together with the second tool limb forming a second conducting path which is electrically separated from the first conducting path, and
wherein the handle members are each attached with respective second pivot joints to the joint bearing without crossing over each other;
the tool limbs are also fastened with the respective first pivot joints without crossing over each other,
the first tool limb is coupled via a first coupling to the first handle member such that a pivot movement about the second pivot joint of the first handle member results in a contrary rotary movement about the first pivot joint of the first tool limb; and
the second tool limb is coupled via a second coupling to the second handle member such that a pivot movement about the second pivot joint of the second handle member results in a contrary rotary movement about the first pivot joint of the second tool limb.

2. The electrosurgical instrument according to claim 1, wherein the first and second pivot joints are rigidly connected to one another.

3. The electrosurgical instrument according to claim 1, wherein the joint bearing comprises two insulator plates between which the first and second pivot joints are arranged.

4. The electrosurgical instrument according to claim 1, further comprising an insulator web provided between the first and second tool limbs and the first and second handle members in the region of the pivot joints in order to insulate the conducting paths relative to one another.

5. The electrosurgical instrument according to claim 4, wherein the insulator web is connected to the joint bearing.

6. The electrosurgical instrument according to claim 1, further comprising a non-conducting synchronisation device provided between the two first pivot joints and/or between the two second pivot joints for mechanical coupling of the first pivot joints and/or second pivot joints, respectively.

7. The electrosurgical instrument according to claim 1, wherein the first and second handle members each comprise an electrical terminal.

8. The electrosurgical instrument according to claim 1, wherein the first and second tool limbs each comprise a groove in which a projection of the respective first and second handle members engages to form the respective first or second coupling.

9. The electrosurgical instrument according to claim 8, wherein the grooves and the projections are configured according to gear toothing.

10. The electrosurgical instrument according to claim 1, wherein the first and second couplings are made from electrically conductive material and respectively comprise a part of the first and second conducting paths.

11. The electrosurgical instrument according to claim 1, wherein the first pivot joints each comprise a receptacle device for detachable fastening of the tool head to the joint bearing.

12. The electrosurgical instrument according to claim 1, wherein the tool head and the handle are made from metal and are partially covered with an insulating layer.

13. A type series for the electrosurgical instrument of claim 1,
comprising at least two tool heads and/or at least two handles which are mutually connectable via the first and second pivot joints and the first and second couplings.

14. The type series according to claim 13, wherein the first and second handle members are configured to be different from each other.

15. The type series according to claim 13, wherein the tool heads comprise at least one tool head for cutting and at least one tool head for clamping.

16. The type series according to claim 14, wherein the first and second handle members have different handle member lengths.

17. The type series according to claim 14, wherein the tool heads comprise at least one tool head for cutting and at least one tool head for clamping.

* * * * *